United States Patent [19]
Stone

[11] Patent Number: 5,512,436
[45] Date of Patent: Apr. 30, 1996

[54] ENHANCEMENT OF POLYNUCLEOTIDE HYBRIDIZATION

[75] Inventor: Timothy Stone, High Wycombe, United Kingdom

[73] Assignee: Amersham International plc, United Kingdom

[21] Appl. No.: 108,578

[22] PCT Filed: Jun. 30, 1992

[86] PCT No.: PCT/EP92/01479

§ 371 Date: Sep. 2, 1993

§ 102(e) Date: Sep. 2, 1993

[87] PCT Pub. No.: WO93/01311

PCT Pub. Date: Jan. 21, 1993

[30] Foreign Application Priority Data

Jul. 1, 1991 [GB] United Kingdom ............... 9114180

[51] Int. Cl.[6] ............................... C12Q 1/68; G01N 1/18
[52] U.S. Cl. .................................. 435/6; 435/180
[58] Field of Search ........................... 435/6, 180, 181, 435/182, 803, 810; 436/528, 821, 826; 935/77, 78; 523/218; 524/817, 819

[56] References Cited

U.S. PATENT DOCUMENTS 4,302,204  11/1981  Wahl et al. .

4,689,294  8/1987  Boguslawski et al. .

FOREIGN PATENT DOCUMENTS 0229442  7/1987  European Pat. Off. .
89/053577  6/1989  WIPO .

OTHER PUBLICATIONS

Zhov et al, Appl. Environ. Microbiol 57:2963–2968 (1991).
Maniatis et al "Molecular Cloning" (1982) pp. 326–327.
JP 2119800, May 7, 1990, "Method of Detection Nucleic Acid . . . " (Derwent Biotech Abs).
Nucleic Acids Research, vol. 14, No. 18, 1986, pp. 7285–7303; N. Casna et al: "Genomic Analysis II: Isolation of High Molecular Weight Heteroduplex DNA Following Differential Methylase Protection and Formamide–Pert Hybridization".

Primary Examiner—W. Gary Jones
Assistant Examiner—Eggerton Campbell
Attorney, Agent, or Firm—Wenderoth, Lind & Ponack

[57]  ABSTRACT

Hybridization buffers, for hybridizing complementary polynucleotides, contain polyvinyl alcohol (MW 1000–20000) and/or polystyrene sulphonic acid (e.g. MW 60000–80000) as a rate enhancer, generally at a concentration of 1–10%. Dextran sulphate, polyethylene glycol and cationic detergents may be additionally present. The method is useful when one of the two complementary polynucleotides is immobilised, or is in in situ hybridizations.

14 Claims, 2 Drawing Sheets

ENHANCEMENT OF POLYNUCLEOTIDE HYBRIDIZATION

This application is a 371 of PCT/EP92/01479, filed on Jun. 30, 1992, which is claiming priority to GB 91144180.4, filed on Jul 1, 1991.

The present invention concerns the hybridization between two complementary polynucleotide segments, and relates in particular to agents for increasing the rate of hybridization and total amount of hybrid formed.

The use of dextran sulphate to increase the rate of DNA hybridization has been reported by a number of workers. U.S. Pat. No. 4,302,204 describes the use of dextran sulphate and other charged polysaccharides to accelerate hybridization reactions in which one of the polynucleotides is covalently attached to a solid phase.

Polyethylene glycol was found by Renz and Kurz (1984) Nucleic Acid Research 12, 3435–3444, to be superior to dextran sulphate for hybridizations with peroxidase labelled nucleic acids. However, subsequent experiments by the author of the present invention where the conditions and concentration of the other components in the hybridization buffer have been altered, showed that dextran sulphate was superior to polyethylene glycol when they were used as the sole hybridization rate enhancers.

U.S. Pat. No. 4,689,294 discloses the use of polyacrylate and polymethacrylate in hybridization buffers, and it states that these two polymers have the following properties:

a) the same rate of hybridization enhancement as dextran sulphate, b) resistance to microbial degradation, c) non-specific binding of probe, to the commonly used nitrocellulose supports, is substantially lower, compared to use of dextran sulphate, d) Polyacrylate is effective at low concentrations and is significantly less expensive than dextran sulphate.

An experiment was performed by the author of the present invention in which it was attempted to hybridize a peroxidase-labelled nucleic acid probe, from solution, to a nucleic acid bound to a charged nylon solid support. It was found that with polyacrylate in the hybridization buffer at 5% concentration, the hybridization of the probe of the complementary nucleic acid bound to the solid support was prevented. Thus, polyacrylates are unsuitable at least for membrane hybridization using peroxidase-labelled probes, and Southern blots made with charged nylon solid support.

The inventor therefore undertook a study to determine if other rate enhancers could be found which would perform as well as dextran sulphate when used at concentrations of 5% (w/v) or less in the hybridization buffer.

BRIEF SUMMARY OF THE INVENTION

It has now been found that polyvinyl alcohol and polystyrene sulphonic acid also increase the rate and/or extent of hybridization of complementary polynucleotide segments. Accordingly in one aspect the present invention provides a method of hybridizing complementary polynucleotides which method comprises maintaining the complementary polynucleotides in a buffered aqueous medium under hybridization conditions, characterized in that the buffered aqueous medium contains polyvinyl alcohol and/or polystyrene sulphonic acid at a concentration to produce an observable increase in the rate and/or extent of hybridization.

In another aspect, the invention provides a hybridization buffer characterized by containing polyvinyl alcohol and/or polystyrene sulphonic acid at a concentration effective to produce an observable increase in the rate and/or extent of hybridization of complementary polynucleotides.

DETAILED DESCRIPTION

The two polymers, polyvinyl alcohol and polystyrene sulphonic acid, may be present in the buffered aqueous medium in anionic form which can be formed in situ or by using a salt of the polymers e.g. Na, K or $NH_4$ salts. A preferred salt is the Na salt. The term polystyrene sulphonic acid is thus used herein to include polystyrene sulphonate.

The hybridization buffer may be of conventional composition, and may also contain various other components which are conventionally used in hybridization media such as surfactants and other polymers.

The polyvinyl alcohol and polystyrene sulphonic acid will normally be present in the hybridization buffer at a concentration of up to 10%, but may be higher, a preferred concentration is from 1 to 10% e.g. about 5%. Normally the molecular weight of these polymers will be between about 1,000 to 1,000,000 daltons. For polyvinyl alcohol the preferred molecular weight is from about 1,000 to 20,000, preferably 5,000 to 15,000 particularly about 10,000. Polyvinyl alcohol is preferably polyvinyl acetate hydrolyzed to an extent of 50% to 100% particularly about 80%. For polystyrene sulphonic acid the preferred molecular weight is from about 60,000 to 80,000 daltons, particularly about 70,000.

These polymers may not be the only hybridization rate enhancers present. They may be used in conjunction with either dextran sulphate or polyethylene glycol. Dextran sulphate of molecular weight 1,000 to 10,000,000 may be used and 500,000 is preferred. Polyethylene glycol of molecular weight 1,000–20,000 may be used and 6,000 is preferred.

The complementary polynucleotide segments may each be all or part of a polynucleotide strand including shorter length oligonucleotides. The polynucleotides segments may include DNA and RNA and derivatives thereof, and hybrids may be formed between DNA/DNA, RNA/RNA or DNA/RNA segments hybridization of which may all be accelerated by the use of the polymers according to this invention.

The present invention is useful whenever it is desired to increase the rate and/or extent of hybridization between two complementary polynucleotide segments in an aqueous medium. The present invention is applicable to hybridization methods in which both of the complementary strands are in solution. The present invention is particularly useful in hybridization methods where one of the complementary polynucleotide segments is immobilized on a solid support. Such systems are commonly used in polynucleotide assay systems wherein a labelled polynucleotide probe complementary to a specific target sequence is brought into contact, in an aqueous medium, with a nucleic acid sample known to contain, or suspected of containing, a polynucleotide including the target sequence. The amount or presence of hybridized probe may then be determined by a suitable assay system depending on the label used. Commonly used labels include radioactive, biotin, fluorescent, enzyme, and hapten. Enzyme (Direct) labels, where the enzyme is covalently linked to the DNA probe, can have detection steps which produce color or a chemiluminescent signal. Hapten labels (Indirect) such as fluorescein, are covalently linked to the probe DNA. These probe molecules can sometimes be detected by fluorescence, but normally require a second labelled moiety such as a specific antibody-enzyme conjugate to enable detection by a colour deposition or a chemiluminescence reaction.

In such assays either the sample nucleic acids may be immobilized prior to formation of the assay medium with the probe or the probe can be the immobilised component. An example of such a system where the nucleic acid sample is immobilized, and for which the present invention is particularly useful, is the Southern blotting technique.

Any solid support conventionally used in such solid phase techniques may be used including nitrocellulose, nylon, charged nylon such as that sold by Amersham International plc under the Trademark Hybond, or polyvinyl difluoride. The solid support is often used in the form of a sheet or membrane, although the exact form is not important to the working of the invention.

The present invention is also applicable to hybridization conducted in situ i.e. wherein one of the polynucleotide segments is part of the nucleic acid which has been immobilized within cell or tissue preparations.

The polymers of the present invention may be combined advantageously with other hybridization rate enhancers, particularly polyethylene glycol or dextran sulphate. It has been observed that certain hybridization rate enhancers not only promote increased rates of hybridization, leading to a greater amount of probe nucleic acid binding to the target nucleic acid, but also promote other interactions leading to more probe nucleic acid binding non-specifically to the solid support.

In this document, polyethylene glycol and polyvinyl alcohol are notable examples of hybridization rate enhancers which give rise to this non-specific binding of probe to the solid support. The present invention shows that either dextran sulphate or polystyrene sodium sulphonate may be used in combination with the other two rate enhancers to reduce this non-specific binding. A proteinaceous blocking agent may also be included in the medium to prevent non-specific binding of the probe to the solid support.

Typically dextran sulphate has been used at a concentration of around 10%. Many buffer formulations which contain dextran sulphate at concentrations >5% separate into two phases. This adversely affects the performance of the buffer as a hybridization medium. Polystyrene sodium sulphonate (PSSA) with or without polyethylene glycol in the optimized buffer formulations mentioned herein, has no such problem. Thus, this can be considered to be an advantage over dextran sulphate.

Polyvinyl alcohol and polystyrene sulphonic acid may be included with dextran sulphate when used in such typical concentrations. However it is also found that a significant improvement is obtained when dextran sulphate is included at much lower amounts, e.g. about 0.5% but may be from 0.1 to 10%.

Polyethylene glycol is another hybridization rate enhancer that may advantageously be used in conjunction with polyvinyl alcohol and polystyrene sulphonic acid. Preferred concentrations of polyethylene glycol are 1 to 25%, particularly 5 to 10%.

Reduction of non-specific binding to a solid support may be achieved by adding to the hybridization buffer a cationic detergent, preferably at a concentration of 0.02% to 2%. Suitable cationic detergents include cetyl trimethylammonium bromide and cetyl pyridinium chloride.

The following Examples illustrate the invention.

Six labelling methods with their corresponding detection methods were used. The detailed protocols can be found in various products from Amersham International plc. * indicates trade marks of Amersham International plc.

Method 1

*ECL direct nucleic acid labelling and detection system RPN3000.

Method 2

*Megaprime DNA labelling system RPN1606.

Method 2a

Rapid hybridization system - *Multiprime RPN1517.

Method 3

*ECL random prime labelling and detection system RPN3030.

Method 4

3'-End labelling kit N4020.

Method 5

*Paired promoter SP6 system RPN2006.

In the Examples, standard saline citrate is abbreviated to SSC, and sodium dodecyl sulphate is abbreviated to SDS.

The results were recorded as:

a) Luminographs or autoradiographs on X-ray film or b) Images on a Charge-Coupled-Device (CCD) camera.

Luminographs and autoradiographs are not included here as they would not reproduce well in a patent specification.

The images on a CCD camera can be interpreted/analysed by a computer which enables accurate measurements of the light emitted during a non-radioactive (light generating) detection.

Concentrations are given as % w/v.

BRIEF DESCRIPTION OF THE DRAWINGS

FIG. 1 shows the difference in the rate of hybridization and the total amount of DNA hybridized, for different rate-enhancers.

FIGS. 2 and 3 show the difference in rate of hybridization and total amount of DNA hybridized, for different buffer formulations, using a $^{32}$P-labelled probe and a fluorescein-labelled probe, respectively.

Examples 1 to 3 are improved descriptions of the experiments reported in Examples 1 to 3 of the priority application.

EXAMPLE 1

To determine the difference in the rate of hybridization and the total amount of DNA hybridized, when using different rate-enhancers.

Materials/Methods

The Core Buffer for this Example is:

6M Urea, 120mM Tris/HCl pH5.0, 0.4% SDS, 0.5M NaCl, 5% Blocking agent

The following buffers were used as the hybridization media for hybridizing peroxidase labelled Lambda Hind III DNA probe at 10 ng/ml to Lambda Hind III DNA Southern blots on Hybond-N+:

Buffer A=Core Buffer+5% Dextran Sulphate.

Buffer B=Core Buffer+5% Polystyrene sodium sulphonate.

Buffer C=Core Buffer+5% Polyvinyl alcohol +0.5% Dextran Sulphate.

Buffer D=Core Buffer+No rate-enhancer.

There were 1, 100 and 1000pg loadings on the blots.

Method 1 was used.

The hybridizations were carried out for different periods of time.

Results/Conclusions

Figure 1:
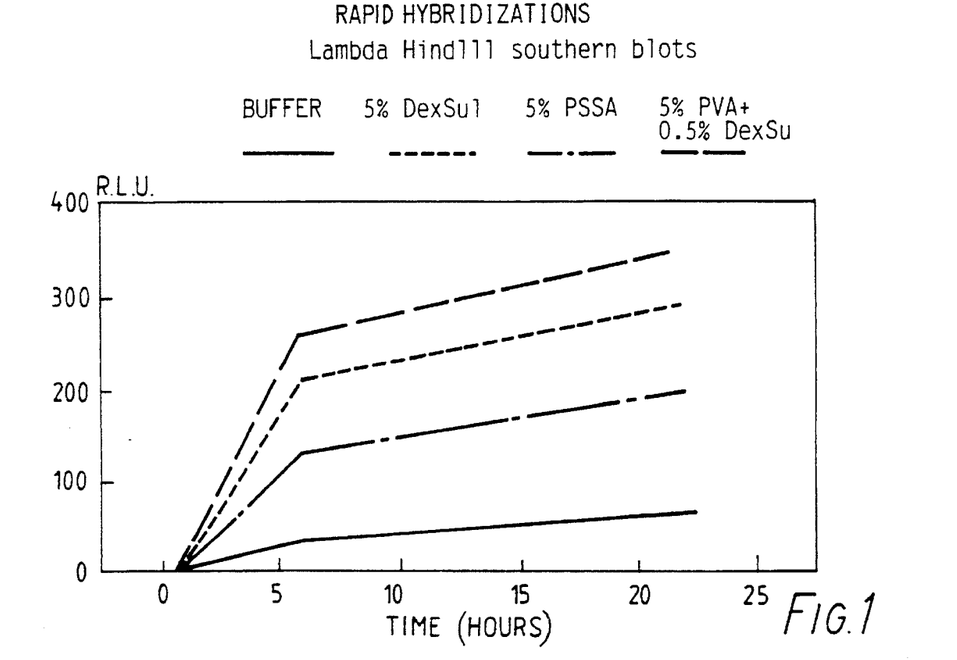
FIGS. 1, 2 and 3 are graphs showing the hybridization kinetics obtained in Examples 1, 11 and 12 respectively.

The results were recorded by a CCD camera as 5 minute exposures. The light emitted from the 4 kb band of the 1 ng loading of Lambda Hind III on the blots was analyzed. The light emitted due to probe bound non-specifically to the solid support was subtracted. The results are presented as a graph in FIG. 1.

All buffers containing the different rate-enhancers show a significant increase in the rate of hybridization over that obtained with the buffer which does not contain rate-enhancer.

It has been found that the 0.5% dextran sulphate added to the buffer containing polyvinyl alcohol has the benefit of reducing the amount of probe binding non-specifically to the solid support.

All buffers containing rate-enhancer allow a greater amount of probe to bind to the target than the buffer containing no rate-enhancer, thus giving greater signal strength.

EXAMPLE 2

The effect of using different hybridization rate-enhancers with Southern blots made with different support materials, and application to single copy gene detection.

Materials/Methods

The Core Buffer for this Example is: 6M Urea, 120 mM Tris/HCl pH 8.0, 0.4% SDS, 0.5 M NaCl, 5% Blocking agent The following buffers were used as the hybridization media for hybridizing peroxidase labelled N-ras insert DNA probe at 10 ng/ml to Human genomic DNA Southern blots on different Hybond membranes:

Buffer A=Core Buffer+5% Dextran Sulphate

Buffer B=Core Buffer+5% Polyvinyl alcohol

Buffer C=Core Buffer+5% Polystyrene sodium sulphonate

There were 5, 2 and 1 μg loadings on the blots.

Method 1 was used.

The hybridization was carried out for 16 hours.

Results/Conclusions

The results were recorded as luminographs (30 minute exposures).

The results obtained with the buffers containing dextran sulphate and polystyrene sodium sulphonate are comparable in this application on Hybond-N (an uncharged nylon membrane) and Hybond-ECL (a pure nitrocellulose membrane).

However, on *Hybond-N+ (a positively-charged nylon membrane) the stringency of the hybridizations with the dextran sulphate and polyvinyl alcohol buffers is poor compared to that of the hybridization with the polystyrene sodium sulphonate buffer. Thus, the polystyrene sodium sulphonate buffer has the advantage of giving results with better stringency than the other two buffers.

EXAMPLE 3

To determine the difference in the amount of hybridization that occurs with buffers containing Polystyrene sodium sulphonate and Polyvinyl alcohol.

Materials/Methods

The Core Buffer for this Example is:

6M Urea, 120 mM Tris/HCl pH 8.0, 0.4% SDS, 0.5M NaCl, 5% Blocking agent

The following buffers were used as the hybridization media for hybridizing peroxidase labelled Lambda Hind III DNA probe at 20 ng/ml to Lambda HindIII DNA Southern blots on Hybond-N+:

Buffer A=Core Buffer+12.5% glycerol+1% Polyvinyl pyrollidone+4 mM EDTA+0.02% Ficoll 400+ 0.02% BSA (Fraction V)+6% Polyethylene glycol.

Buffer B=Core Buffer+5% Polystyrene sodium sulphonate.

Buffer C=Core Buffer+5% Polyvinyl alcohol

There were 10, 100 pg loadings on the blots.

Method 1 was used.

The hybridizations were carried out for hours.

Results/Conclusions

The result was recorded as a luminograph (30 minute exposure).

The total amount of hybrid formed after a two hour hybridization with the polystyrene sodium sulphonate and polyvinyl alcohol buffers appears to be equivalent, and is considerably more than the amount formed with the other buffer. However, the polyvinyl alcohol buffer has allowed more probe to bind nonspecifically to the charged nylon membrane.

EXAMPLE 4

A comparison of hybridization buffers formulated with Polystyrene sodium sulphonate, Polyethylene glycol and Dextran sulphate.

Materials/Methods

The Core Buffer for this Example is:

5×SSC, 0.1% SDS

The following buffers were used as the hybridization media for hybridizing $^{32}$P-labelled N-ras insert DNA probe at approx. 2 ng/ml to Hind III Human genomic DNA Southern blots on Hybond-N+:

Buffer A=Core Buffer+5% Polystyrene sodium sulphonate.

Buffer B=Core Buffer+10% Polystyrene sodium sulphonate.

Buffer C=Core Buffer+5% Polystyrene sodium sulphonate+5% Polyethylene glycol.

Buffer D=Core Buffer+5% Dextran sulphate.

Buffer E=Core Buffer+10% Dextran sulphate.

Buffer F=Core Buffer+5% Dextran sulphate 5% Polyethylene glycol.

There were 5, 2, and 1 Ng loadings on the blots.
Method 2 was used.
The hybridizations were carried out for 1 hour.

Results/Conclusions

The result was recorded as an autoradiograph (17 hour exposure).

The total amount of hybridization that had occured using each of the buffers can be summarized as follows:

Buffer A was equivalent to Buffer D but allowed less hybridization than Buffer B, which was equivalent to Buffer E and Buffer F. The buffer containing polyethylene glycol and polystyrene sodium sulphonate Buffer C, allowed the most amount of hybridization to occur.

|  |  |  |
|---|---|---|
| Buffer C | Buffer B >> or >> Buffer E or Buffer F | Buffer A or Buffer D |

It can be concluded that polystyrene sodium sulphonate or dextran sulphate can be used in combination with polyethylene glycol to increase the total amount of hybrid formed during a hybridization, but polystyrene sodium sulphonate works better than dextran sulphate when used in combination with polyethylene glycol.

EXAMPLE 5

The effect of changing polystyrene sodium sulphonate and polyethylene glycol concentrations when they are used together as rate-enhancers.

Materials/Methods

The Core Buffer for this Example is:
5'SSC, 0.1% SDS, 10% Polyethylene glycol

The following buffers were used as the hybridization media for hybridizing $^{32}$P-labelled N-ras insert DNA probe at approx. 2ng/ml to Hind III Human genomic DNA Southern blots on Hybond-N+:

PSSA = Polystyrene sodium sulphonate
Buffer A=Core Buffer
Buffer B=Core Buffer+2% PSSA
Buffer C=Core Buffer+4% PSSA
Buffer D=Core Buffer+5% PSSA
Buffer E=Core Buffer+6% PSSA
Buffer F=Core Buffer+8% PSSA
Buffer G=Core Buffer+5% PSSA+ 2.5% Polyethylene glycol.
Buffer H=Core Buffer+5% PSSA+ Polyethylene glycol There were 5, 2, and 1 µg loadings on the blots.
Method 2 was used.
The hybridizations were carried out for 1 hour.

Results/Conclusions

The results were recorded as autoradiographs (a 17 hour exposure and a 5 day exposure).

The amount of hybridization increases with increasing polystyrene sodium sulphonate concentration when a 10% polyethylene glycol concentration is maintained. The maximum amount of hybridization occurs with 10% polyethylene glycol+5% polystyrene sodium sulphonate (Buffer D). A greater concentration of either of these rate-enhancers (Buffers E, F, G, or H) reduces the final amount of probe that hybridizes to the target, although this concomitantly reduces the amount of probe that binds non-specifically to the solid support.

EXAMPLE 6

The effect of SSC concentration variation on the performance of a hybridization buffer containing 10% polyethylene glycol and 5% polystyrene sodium sulphonate.

Materials/Method

The Core Buffer for this Example is:
10% Polyethylene glycol, 5% Polystyrene sodium sulphonate.

The following buffers were used as the hybridization media for hybridizing $^{32}$P-labelled N-ras insert DNA probe at approx. 2 ng/ml to Hind III Human genomic DNA Southern blots on Hybond-N+:

Buffer A=Core Buffer.
Buffer B=Core Buffer+5×SSC.
Buffer C=Core Buffer+6×SSC.

There were 5, 2, and 1 µg loadings on the blots.
Method 2 was used.
The hybridizations were carried out for b 1hour.

Results/Conclusions

The results were recorded as autoradiographs (17 hour exposures).

Buffer B allows the greatest amount of hybridization to occur. Buffer A is poor because it allows the greatest amount of non-specific binding of probe to solid support to occur. Buffer C is poor even though there is virtually no non-specific binding of probe to the solid support, this buffer formulation prevents hybridization from occurring to any great extent.

EXAMPLE 7

The effect of different rate-enhancers on the hybridization of a probe labelled with a non-radioactive reporter molecule.

Materials/Methods

The Core Buffer for this Example is:
5×SSC, 0.1% SDS.

The following buffers were used as the hybridization media for hybridizing Fluorescein-dUMP labelled Lambda Hind III DNA probe at 10 ng/ml to Lambda Hind III DNA dot blots on Hybond-N+:

PSSA=Polystyrene sodium sulphonate.
Buffer A=Core Buffer+5% PSSA+ 0.5% Blocking agent
Buffer B=Core Buffer+5% PSSA+5% Dextran sulphate+ 0.5% Blocking agent.
Buffer C=Core Buffer+5% Dextran sulphate +0.5% Blocking agent
Buffer D=Core Buffer+5% PSSA+ 10% Polyethylene glycol.

Buffer E=Core Buffer+5% PSSA+ 10% Polyethylene glycol+0.5% Blocking agent.

Buffer F=Core Buffer+10% PSSA+ 10% Polyethylene glycol

Buffer G=Core Buffer+10% PSSA+ 10% Polyethylene glycol+0.5% Blocking agent.

There were

| 100, | 250, | 500, | 1000, | 5000fg |
|------|------|------|-------|--------|
| 0,   | 1,   | 5,   | 10,   | 50fg   | loadings on the blots.

Method 3 was used.

The hybridizations were carried out for 16 hours.

Results/Conclusions

The result was recorded as a luminograph (30 minute exposure).

Buffer C containing 5% dextran sulphate was a buffer that had been optimized for use with this particular probe type. It appears to be equivalent to Buffer A which is essentially the same formulation, but 5% polystyrene sodium sulphonate is used in place of dextran sulphate. Better sensitivity is achieved by using a Buffer B which contains both dextran sulphate and polystyrene sodium sulphonate each at 5% concentrations.

The buffer formulations that allow the greatest amount of hybridization to occur are those of Buffers D and E. Both of these buffers contain 5% polystyrene sodium sulphonate and 10% polyethylene glycol. The addition of Blocking agent in Buffer E appears to have increased the amount of probe that has bound non-specifically to the membrane.

Buffers F and G which have the greatest concentrations of polystyrene sodium sulphonate at 10%, appear to allow less hybridization of the probe to occur. However, the reduction of hybridization appears to have been limited in Buffer G by the inclusion of 0.5% Blocking agent.

EXAMPLE 8

Reduction of non-specific binding of labelled probe to nylon solid support by the addition of cationic detergent.

Materials/Methods

The Core Buffer for this Example is: 10% Polyethylene glycol, 5% polystyrene sodium sulphonate, 5×SSC.

The following buffers were used as the hybridization media for hybridizing $^{32}$P-labelled N-ras insert DNA probe at approx. 2 ng/ml to Hind III Human genomic DNA Southern blots on Hybond-N+:

CTAB=Cetyl trimethyl ammonium bromide

Buffer A=Core Buffer

Buffer B=Core Buffer+0.05% CTAB

Buffer C=Core Buffer+0.1% CTAB

Buffer D=Core Buffer+0.5% CTAB

Buffer E=Core Buffer+1.0% CTAB

There were 5, 2, and 1 µg loadings on the blots.

Method. 2 was used.

The hybridizations were carried out for 1 hour.

Results/Conclusions

The results were recorded as two autoradiographs (3 day and 7 day exposures).

The CTAB reduces the amount of non-specific binding to the solid support at concentrations greater than 0.05%. The most significant reduction occurs at concentrations between 0.1% and 0.5%. There is no further reduction of the non-specific binding at 1.0% concentration. The optimum cationic detergent concentration appears to be between 0.1% and 0.5% because, even though 0.5% CTAB significantly reduces the non- specific binding, it also prevents hybridization of the probe from occurring to the same extent as in the buffer containing 0.1% CTAB.

EXAMPLE 9

Reduction of non-specific binding of labelled probe to nylon solid support by the addition of cationic detergent.

Materials/Methods

The Core Buffer for this Example is:

10% Polyethylene glycol, 5% polystyrene sodium sulphonate, 5×SSC.

The following buffers were used as the hybridization media for hybridizing $^{32}$P-labelled N-ras insert DNA probe at approx. 2 ng/ml to Hind III Human genomic DNA Southern blots on Hybond-N+:

CTAB=Cetyl trimethyl ammonium bromide.

CPC=Cetyl pyridinium chloride.

Buffer A=Core Buffer.

Buffer B=Core Buffer+0.2% CTAB.

Buffer C=Core Buffer+0.2% CPC.

There were 5, 2, and 1 µg loadings on the blots.

Method 2 was used. Also another probe labelling method was used (Method 2a) where the DNA to be labelled was denatured separately before the addition of primer, the rest of the method is identical to Method 2.

Six hybridizations were carried out for 1 hour.

(Probe labelled by each of the methods above was added to each of the three buffers above).

Results/Conclusions

The results were recorded as two autoradiographs (5 day exposures).

In this example there was an insignificant amount of non-specific binding to the solid support with the probe that was labelled by Method 2 (FIG. 9a) with all three buffers. However, there was significantly more non-specific binding of the probe labelled by Method 2a to the solid support in the buffer with no cationic detergent present (Buffer A) (See FIG. 9b). The cationic detergents in buffers B and C at 0.2% concentrations, have significantly reduced the amount of probe bound non-specifically to the nylon solid support, without affecting the extent of hybridization to the target DNA.

This example shows that there is no apparent difference in the extent of hybridization to Southern blots in the presence or absence of 0.2% cationic detergent, whether it is CTAB or CPC, but that cationic detergents can reduce the level of non-specific binding to the solid support.

EXAMPLE 10

Application of rate-enhanced buffers to Northern hybridizations.

Materials/Methods

The Core Buffer for this Example is:

10% Polyethylene glycol, 5% polystyrene sodium sulphonate, 5×SSC.

The following buffers were used as the hybridization media for hybridizing $^{32}$P-labelled linearized HSP70 DNA probe at approx. 2 ng/ml to HeLa cell total RNA Northern blots on Hybond-N+:

Buffer A=Core Buffer.

Buffer B=Core Buffer+0.2% Cetyl trimethyl ammonium bromide.

Buffer C=Core Buffer+0.2% Cetyl pyridinium chloride.

There were 500 and 1000 ng loadings of RNA on the blots.

Method 2 was used.

The hybridizations were carried out for 1 hour.

Results/Conclusions

The results were recorded as an autoradiograph (16 hour exposure).

All three buffers have worked well in this Northern hybridization application. There is no significant difference in the amount of probe that has bound non-specifically to the membrane. The use of Cetyl pyridinium chloride appears to be aadvantageous in this example, because Cetyl trimethyl ammonium bromide appears to have reduced the amount of probe hybridizing to the target RNA to a small extent.

EXAMPLE 11

To determine the difference in the rate of hybridization and the total amount of DNA hybridized, when using different buffer formulations with a $^{32}$-labelled probe.

Materials/Methods

The Core Buffer for this Example is:

10% Polyethylene glycol, 5% polystyrene sodium sulphonate, 5×SSC.

The following buffers were used as the hybridization media for hybridizing $^{32}$P-labelled N-ras insert DNA probe at approx. 2 ng/ml to Hind III Human genomic DNA Southern blots on Hybond-N+:

CTAB=Cetyl trimethyl ammonium bromide.

CPC=Cetyl pyridinium chloride.

Buffer A=2 hour Rapid Hybridization Buffer RPN 1518 (Amersham International) containing 10% Polyethylene glycol.

Buffer B=Core Buffer+0.2% CTAB.

Buffer C=Core Buffer+0.2% CPC.

There were 5, 2, and 1 µg loadings on the blots.

Method 2 was used.

The hybridizations were carried out for different periods of time.

Results/Conclusions

Figure 2:
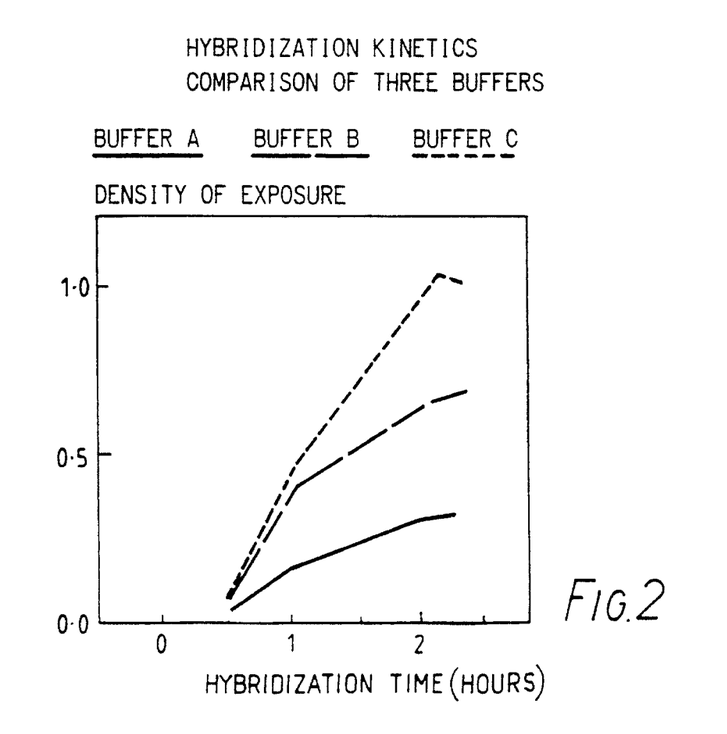

The results were recorded as an autoradiograph (17 hour exposure). The intensity of the bands (amount of probe hybridized) was determined by densitometry. See FIG. 2.

The two buffers B and C which contain 5% Polystyrene sodium sulphonate in addition to 10% Polyethylene glycol allow hybridization to occur at approximately twice the rate of the Buffer A which contains only 10% Polyethylene glycol as a rate-enhancer. Buffer C (with 0.2% CPC) is better than Buffer B (with 0.2% CTAB), because it allows the greatest amount of hybridization to occur in two hours.

EXAMPLE 12

To determine the difference in the rate of hybridization and the total amount of DNA hybridized, when using different buffer formulations with a Fluorescein-labelled probe.

Materials/Methods

The following buffers were used as the hybridization media for hybridizing Fluorescein-dUMP labelled N-ras insert DNA probe at 10 ng/ml to Hind III Human genomic DNA Southern blots on Hybond-N+:

CPC=Cetyl pyridinium chloride.

Buffer A=5% Dextran sulphate+5×SSC+ 0.1% SDS+ 0.5% Blocking agent.

(A dextran sulphate buffer optimized for use with the probe type used in this particular example).

Buffer B=10% Polyethylene glycol+5% Polystyrene sodium sulphonate+5×SSC+0.2% CPC.

(This buffer has been optimized for use with $^{32}$P-labelled probes but has also been used with Fluorescein-labelled probes).

There were 2, 1, and 0.5 µg loadings on the blots.

Method 3 was used.

The hybridizations were carried out for different periods of time.

Results/Conclusions

Figure 3:
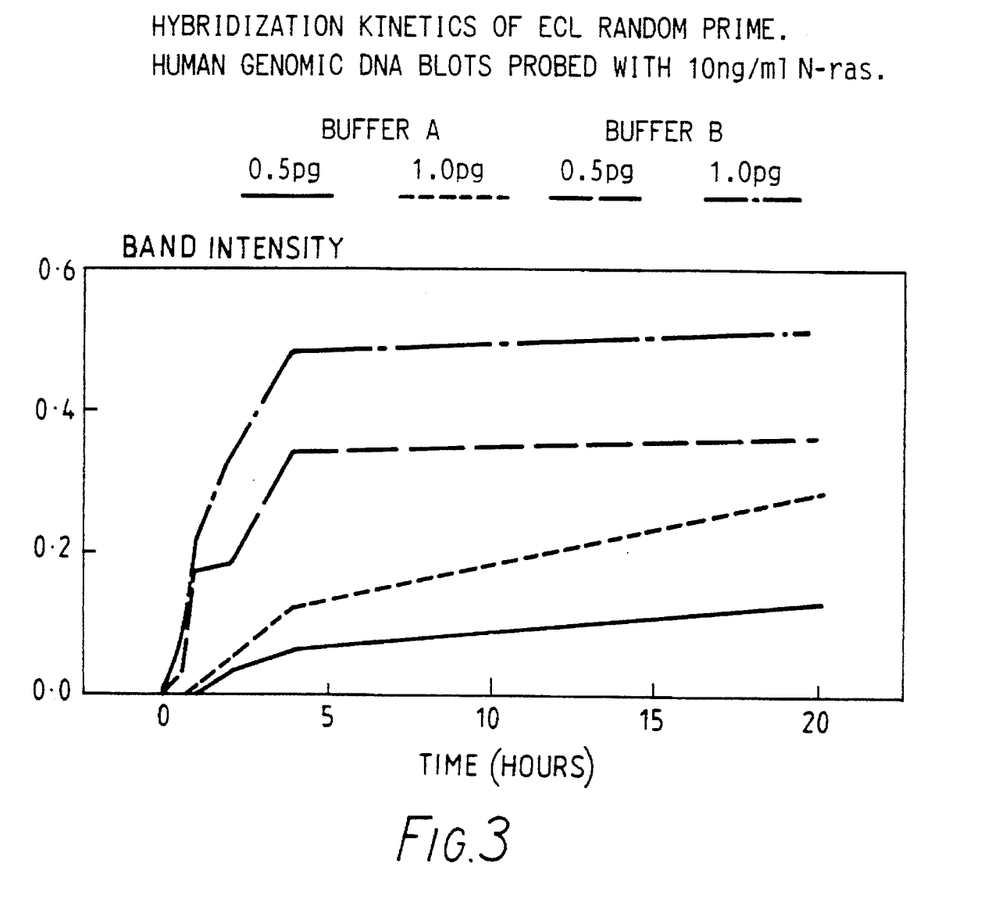

The results were recorded as a luminograph (90 minute exposure). The intensity of the bands (amount of probe hybridized) was determined by densitometry. See FIG. 3.

The rate of hybridization of Buffer B is initially between 6–20 fold faster than that of Buffer A. The results also show that approximately 2–3 fold more probe DNA hybridizes when a combination of 5% polystyrene sodium sulphonate and 10% polyethylene glycol is used. Thus the combination of polystyrene sodium sulphonate and polyethylene glycol is superior to the use of dextran sulphate on its own. This Example in conjunction with Example 11, shows that buffer formulation B of this example is suitable for use with different probe types.

EXAMPLE 13

Application of rate-enhanced hybridization buffer to oligo-nucleotide probes.

Materials/MethodS

The following buffers were used as the hybridization media for hybridizing $^{32}$P-labelled M13 forward sequencing primer oligo-nucleotide DNA probe at 10 ng/ml to M13

DNA dot blots on Hybond-N+:

Buffer A=5×SSC+0.1% Hybridization buffer component (from Amersham's 3'-oligolabelling system RPN 2130)+ 0.02% SDS+0.5% Blocking agent.

Buffer B=10% Polyethylene glycol+ 5% Polystyrene sodium sulphonate+5×SSC+0.2% CPC.

(This buffer has been optimized for use with $^{32}$P-labelled probes but has also been used with Fluorescein-labelled probes)

There were

| | | |
|---|---|---|
| 100, | 200, | 500pg |
| 10, | 20, | 50pg | loadings on the blots.

Method 4 was used.

The hybridizations were carried out for different periods of time.

Results/ConclUSions

The results were recorded as an autoradiograph (5 day exposure).

The rate of hybridization is approximately 2 fold faster in the rate-enhanced Buffer B than that in the simple oligo-nucleotide hybridization buffer Buffer A. When using a specific length of time for the hybridization, the total amount of oligo-nucleotide probe that has bound is also greater with the rate-enhanced buffer (Buffer B). This example shows that the rate of oligo-nucleotide hybridizations can be enhanced by the use of polystyrene sodium sulphonate and polyethylene glycol in the hybridization medium.

EXAMPLE 14

Application of rate enhanced hybridization buffers to in situ hybridization procedures.

Materials/Methods

The following buffers were used as the hybridization media for hybridizing a fluorescein-11-dUTP labelled pro-opiomelano corticotrophin hormone DNA probe (labelled by Method 3) at 100 ng/ml to 8 um rat pituitary sections immobilized on glass microscope slides:

Buffer A=5% polystyrene sodium sulphonate+ 6M Urea+ 120 mM Tris/HCl pH 8.0+0.4% SDS+0.5M NaCl+ 5% blocking agent.

Buffer B=10% Dextran sulphate+50% deionized formamide+0.02% polyvinyl pyrollidone+ 0.02% bovine serum albumin+0.02% Ficoll+4×SSC+ 0.25mg/ml yeast tRNA+ 0.5mg/ml denatured herring sperm DNA.

The hybridizations were carried out for 17 hours at 42° C.

Stringency washes were performed as follows:

(a) 2×SSC, 0.1% SDS for 3×5 minutes at room temperature.

(b) 0.2×SSC, 0.1% SDS for 2×15 minutes at 42° C.

Section blocking, antibody incubations and washes were performed as in Method 3. The antibody used was an alkaline phosphatase conjugate of anti-fluorescein used at 1:1000 of the stock supply.

Detection was through alkaline phosphatase substrates NBT/BCIP which produce a blue-colored precipitate at the site of hybridization.

Results/Conclusions

Detected sections were viewed through a Zeiss microscope using ×10 and ×40 objective lenses. Signal could be seen in the correct areas of the section. The results from the two different hybridization buffers were equivalent. Buffer A therefore behaves in the same manner as a buffer containing dextran sulphate as a rate-enhancer.

EXAMPLE 15

Application of rate enhanced hybridization buffers to in situ hybridization procedures.

Materials/Methods

The following buffers were used as the hybridization media for hybridizing a $^{35}$S-UTP labelled pro-opiomelano corticotrophin hormone RNA probe (labelled using the Paired promoter SP6 system RPN 2006 Amersham International plc.) at 10 ng/ml to 8 um rat pituitary sections immobilized on glass microscope slides:

Buffer A=5% polystyrene sodium sulphonate+ 6M Urea+ 120 mM Tris/HCl pH 8.0+0.4% SDS+0.5M NaCl+ 5% blocking agent.

Buffear B=10% Dextran sulphate+50% deionized formamide+0.02% polyvinyl pyrollidone+ 0.02% bovine serum albumin+0.02% Ficoll+4×SSC+ 0.25 mg/ml yeast tRNA+ 0.5mg/ml denatured herring sperm DNA.

The hybridizations were carried out for 17 hours at 55° C.

Stringency washes were performed as follows:

(a) 2×SSC, 0.1% SDS for 3×5 minutes at room temperature.

(b) 0.1×SSC, 0.1% SDS for 2×15 minutes at 55° C.

Detection was achieved by coating the slides with nuclear track photographic emulsion and leaving to expose in the dark at 4° C. for the required length of time (typically 4–7 days).

Results/Conclusions

Detected sections were viewed through a Zeiss microscope using ×10 and ×40 objective lenses. Signal could be seen in the correct areas of the section as deposited silver grains overlaying the tissue morphology. The results from the two different hybridization buffers were equivalent. Buffer A therefore behaves in the same manner as a buffer containing dextran sulphate as a rate-enhancer.

METHOD 1

Preparation of probe

100ng labelling reactions were carried out using the ECL direct nucleic acid labelling and detection systems RPN 3000 (Amersham International plc) .

1.1 Thaw out the DNA to be labelled.

1.2 Denature 10 µl of DNA (10 ng/µl in water) in microcentrifuge tube by heating to 95°–100° C. in boiling water bath for 5 minutes. Place on ice for 5 minutes. Centrifuge tube in microfuge to collect reagents at the bottom of the tube.

1.3 Add an equal volume of labelling reagent (charge-modified horseradish peroxidase) to each tube (10 µl). Mix well.

1.4 Add a volume of glutaraldehyde solution equivalent to that of the volume of labelling reagent, mix well.

1.5 Incubate the tubes at 37° C. for 10 minutes.

1.6 Place the reactions on ice for up to 30 minutes until ready for addition to the hybridizations.
1.7 Pool all reactions.
1.8 Labelled probe DNA can be stored at −20° C. at this point if required by addition of glycerol to a 50% final concentration.

Hybridization 1.9 Prewarm the hybridization buffers to 42° C.
1.10 Prehybridize the blots in the hybridization buffers. The volume used should be 0.25ml/cm² of membrane. However the minimum volume needed in a 5.5×3.5 cm box is 5 mls and in a 7.5×4.5 cm box is 10 mls. Add the volume of buffer required to the box. Lay the blot onto the surface of the buffer, allow it to prewet then submerge. Ensure that the blots are completely covered by the buffer.
1.11 Incubate at 42° C. for 30 minutes in a shaking waterbath.
1.12 Add labelled probe to a final concentration of 10 ng/ml to each box (ie add 30 µl of labelled probe to 10 mls of buffer). Mix well by tilting box from side to side or by gentle agitation.
1.13 Hybridize for required period at 42° C. in a shaking waterbath.

Stringency Washes 1.14 Carefully remove the blots from the boxes using forceps and wash all blots together for the following series of stringency washes. A minimum volume of 100 ml is required for each of these washes which should be carried out in a shaking waterbath. The first stringency wash buffer (a) should be prewarmed to 42° C. before use.
a) 6M Urea, 0.5'SSC, 0.4% SDS, 2×20 minutes at 42° C.
b) 2×SSC, 2×5 minutes at room temperature.

ECL Detection 1.15 Mix an equal volume of detection reagent 1 with detection reagent 2 to give sufficient to cover the blots ( 0.125ml/cm² is recommended ).
1.16 Drain blots and lay DNA side up onto a piece of Saran Wrap. Add the mixed ECL reagents to the surface of the blots and leave for one minute.
1.17 Drain blots on tissue and lay DNA side down, onto a fresh piece of Saran Wrap (trademark of Dow Chemicals). Fold the excess Saran Wrap over the back of the blots, smoothing out any air pockets.
1.18 Expose the blots to autoradiographic X-ray film for 30 minutes.
1.19 Process the film using a film processor.

METHOD 2

Preparation of probe 25 ng labelling reactions were carried out using the Megaprime Labelling Kit RPN 1606 (Amersham International plc).
2.1 Thaw out the DNA to be labelled, labelling buffer and primer solution in an ice bath. Thaw out the $(a-^{32}P)$-dCTP in a hood. Do not remove the enzyme from the −20° C. freezer until it is required.
2.2 Dilute the DNA to 10 ng/µl using PF water.
2.3 Put 2.5 µl of DNA (25 ng) into each microcentrifuge tube followed by 5 µl of primer and then 25.5 µl of water.
2.4 Denature this by heating to 95°–100° C. in a boiling water bath for 5 minutes. Then place at RT for a further 5 minutes. Centrifuge tubes in microfuge to collect reagents at the bottom of the tube.
2.5 Add 10 µl of labelling buffer to each tube at RT.
2.6 Transfer tubes to a fume hood with appropriate screening from $^{32}P$ and add,

| | |
|---|---|
| $(a-^{32}P)$-dCTP PB10205 | 5 µl |
| Enzyme solution | 2 µl |

2.7 Mix gently by pipetting slowly up and down. (Avoid vigorous mixing as severe loss of enzyme activity may result). Cap the tubes.
2.8 Centrifuge the tubes for 3 seconds in a microfuge to collect the reagents at the bottom of the tubes.
2.9 Incubate the tubes at 37° C. for 10 minutes.
2.10 Stop the reactions by addition of 5 µl of 0.5M EDTA (pH 8.0) to each tube.
2.11 Pool all reactions.
2.12 Check the % incorporation by any suitable method.

Hybridization 2.13 Prewarm the hyb buffers to 65° C.
2.14 Prehybridize the blots in the hybridization buffers The volume used should be 0.25 ml/cm² of membrane. However the minimum volume needed in a 5.5×3.5 cm box is 5 mls and in a 7.5×4.5 cm box is 10 mls. Add the volume of buffer required to the box. Lay the blot onto the surface of the buffer, allow it to prewet then submerge. Ensure that the blots are completely covered by the buffer.
2.15 Incubate at 65° C. for 15 mins in a shaking waterbath.
2.16 Denature the probe at 95°–100° C. for 5 mins. in a boiling water bath and chill on ice.
2.17 Add 14 µl of freshly denatured probe per 5 ml of hybridization buffer (approximately 2 ng/ml). Add the probe as far away from the blot as possible. Mix well by tilting box from side to side or by gentle agitation.
2.18 Hybridize for 2 hours at 65° C. in a shaking waterbath.
Stringency Washes
2.19 Carefully remove the blots from the boxes using forceps and wash all blots together for the following series of stringency washes. (Agitation in 100 ml volume is required for each of these washes. )
a) 2×SSC, 0.1% SDS, 20 minutes at room temperature.
b) 0.5×SSC, 0.1% SDS, 2×15 minutes 65° C. (solutions should be prewarmed)

Detection 2.20 Dry the blots on filter paper. Wrap the damp blots in Saran Wrap. Smooth out any air bubbles using a tissue as these will hinder autoradiography.
Expose to X-ray film with 2 intensifying screens and place into a −70° C. freezer, for 16 hours.
2.21 Process the film using a film processor.
2.22 Expose another sheet of X-ray film as above for several days and process.

METHOD 3

Preparation of probe 50 ng labelling reactions were carried out using the ECL random prime labelling and detection systems RPN 3030 (Amersham International plc).

3.1 Thaw out the DNA to be labelled and the nucleotide mix, primer solution and water from the kit, in an ice bath. Do not remove the enzyme from the −20° C. freezer until it is required.

3.2 Denature 5 μl of DNA (10 ng/μl) in microcentrifuge tube by heating to 95°–100° C. in boiling water bath for 5 minutes. Place on ice for 5 minutes. Centrifuge in microfuge to collect reagents at the bottom of the tube.

3.3 Add to each tube:

5 μl primer mix

10 μl nucleotide mix (contains Fl-dUTP, dATP, dCTP, dGTP and dTTP)

29 μl water

1 μl enzyme solution 3.4 Mix gently by pipetting slowly up and down. (Avoid vigorous mixing as severe loss of enzyme activity may result). Cap the tubes.

3.5 Incubate the tubes at 37° C. for 60 minutes.

3.6 Stop the reactions by addition of 2 μl of 0.5M EDTA (pH 8.0) to each tube.

3.7 Pool all reactions.

3.8 Labelled probe DNA can be stored at −20° C. at this point if required.

Hybridization 3.9 Prewarm the hybridization buffers to 60° C.

3.10 Prehybridize the blots in the hybridization buffers. The volume used should be 0.25 ml/cm$^2$ of membrane. However the minimum volume needed in a 5.5×3.5 cm box is 5 mls and in a 7.5×4.5 cm box is 10 mls. Add the volume of buffer required to the box. Lay the blot onto the surface of the buffer, allow it to prewet then submerge. Ensure that the blots are completely covered by the buffer.

3.11 Incubate at 60° C. for 30 minutes in a shaking waterbath.

3.12 Denature the probe at 95°–100° C. for 5 mins. in a boiling water bath and chill on ice.

3.13 Add denatured probe to a final concentration of 10 ng/ml to each box (ie add 25 μl of denatured probe to 10 mls of buffer). Add the probe as far away from the blot as possible. Mix well by tilting box from side to side or by gentle agitation.

3.14 Hybridize for 2 hours at 60° C. in a shaking waterbath.

Stringency Washes 3.15 Carefully remove the blots from the boxes using forceps and wash all blots together for the following series of stringency washes. A minimum volume of 100 ml is required for each of these washes which should be carried out in a shaking waterbath. The stringency wash buffers should be prewarmed to 60° C. before use.

a) 1×SSC, 0.1% SDS, 15 minutes at 60° C.

b) 0.5×SSC, 0.1% SDS, 15 minutes at 60° C.

Antibody blocking, incubation and washes 3.16 Rinse all the blots in antibody wash buffer for 8–10 minutes at room temperature.

3.17 Incubate all blots together in 100 ml block buffer for 60 minutes at room temperature with gentle agitation. Ensure all blots are moving freely.

3.18 Rinse blots in antibody wash buffer for 1 minute at room temperature.

3.19 Dilute the anti-fluorescein antibody-HRP conjugate 1000-fold in antibody incubation buffer i.e. 100 μl in 100ml. The volume required should be at least equivalent to that used for the hybridizations i.e. 0.25 ml/cm$^2$ 3.20 Incubate the blots in the diluted antibody conjugate for 60 minutes at room temperature with gentle agitation.

3.21 Remove unbound conjugate by washing for 2×10 minutes followed by 2×5 minutes in wash solution at room temperature with gentle agitation. An excess volume (2 ml/cm$^2$) is used (all filters can be washed together in approximately 100 ml per wash).

ECL Detection 3.22 Mix an equal volume of detection reagent 1 with detection reagent 2 to give sufficient to cover the blots (0.125ml/cm$^2$ is recommended).

3.23 Drain blots and lay DNA side up onto a piece of Saran Wrap. Add the mixed ECL reagents to the surface of the blots and leave for one minute.

3.24 Drain blots on tissue and lay DNA side down, onto a fresh piece of Saran Wrap. Fold the excess Saran Wrap over the back of the blots, smoothing out any air pockets.

3.25 Expose the blots to X-ray film for 60 minutes.

3.26 Process the film using a film processor.

METHOD 4

Preparation of probe 10 pmole labelling reactions were carried out using the 3'-End Labelling Kit N4020 (Amersham International plc).

4.1 Thaw out the oligo-nucleotide DNA to be labelled (for example M13 forward sequiencing primer) and the labelling buffer in an ice bath. Thaw out the (a-$^{32}$P)-dATP in a hood. Do not remove the enzyme from the −20° C. freezer until it is required.

4.2 Dilute the DNA to 1 pmole/μl using double distilled water.

4.3 Put 10 μL of DNA (10 pmoles) into each microcentrifuge tube followed by 25 μl of water.

4.4 Add 5 μl of labelling buffer to each tube at RT.

4.5 Transfer tubes to a fume hood with appropriate screening from $^{32}$P and add,

| (a-$^{32}$P)-dATP PB10204 | 5 μl |
| Terminal deoxynucleotidyl transferase | 5 μl |

4.6 Mix gently by pipetting slowly up and down. (Avoid vigorous mixing as severe loss of enzyme activity may result). Cap the tubes.

4.7 Centrifuge the tubes for 3 seconds in a microfuge to collect the reagents at the bottom of the tubes.

4.8 Incubate the tubes at 37° C. for 45 minutes.

4.9 Stop the reactions by addition of 5 μl of 0.5M EDTA (pH 8.0) to each tube.

4.10 Pool all reactions.

4.11 Check the % incorporation by any suitable method.

Hybridization 4.12 Prewarm the hybridization buffers to 42° C.

4.13 Prehybridize the blots in the hybridization buffers The volume used should be 0.25 ml/cm$^2$ of membrane. However the minimum volume needed in a 5.5×3.5 cm box is 5 mls and in a 7.5×4.5 cm box is 10 mls. Add the volume of buffer required to the box. Lay the blot onto the surface of the buffer, allow it to prewet then submerge. Ensure that the blots are completely covered by the buffer. 4.14 Incubate at 42° C. for 15 mins in a shaking waterbath.

4.15 Add 5 μl of probe per 5ml of hybridization buffer (approximately 10 ng/ml). Add the probe as far away from the blot as possible. Mix well by tilting box from side to side or by gentle agitation.

4.16 Hybridize for the required time at 42° C. in a shaking waterbath.

Stringency Washer 4.17 Carefully remove the blots from the boxes using forceps and wash all blots together for the following series of stringency washes. (Agitation in 100 ml volume is required for each of these washes.)
 a) 5×SSC, 0.1% SDS, 2×5 minutes at room temperature
 b) 1×SSC, 0.1% SDS, 2×15 minutes at 42° C. (solutions should be prewarmed)

Detection 4.18 Dry the blots on filter paper. Wrap the damp blots in Saran Wrap. Smooth out any air bubbles using a tissue as these will hinder autoradiography.
Expose to X-ray film with 2 intensifying screens and place into a −70° C. freezer, for 16 hours.

4.19 Process the film using a film processor.

4.20 Expose another sheet of X-ray film as above for several days and process.

I claim:

1. The method of enhancing hybridization of complementary polynucleotides which method comprises providing the complementary polynucleotides in a buffered aqueous medium under hybridization conditions, wherein the buffered aqueous medium contains polystyrene sulphonic acid free in solution and unattached to a nucleic acid probe or target nucleic acid, and said polystyrene sulphonic acid having a molecular weight of between about 1,000 and 1,000,000 daltons.

2. The method as claimed in claim 1 wherein one of the complementary polynucleotides is immobilized on a solid support.

3. The method as claimed in claim 2 or claim 1, wherein the polynucleotide immobilized on the solid support is DNA or RNA.

4. The method as claimed in claim 2 or claim 1, wherein the solid support is in the form of a membrane.

5. The method as claimed in claim or claim 1, wherein the solid support is of nitrocellulose, nylon, charged nylon or polyvinyl difluoride.

6. The method as claimed in claim 1, wherein the hybridization is an in situ hybridization.

7. The method as claimed in claim 1, wherein one of the complementary polynucleotides is a labelled polynucleotide probe.

8. A hybridization buffer containing polystyrene sulphonic acid free in solution and unattached to a nucleic acid probe or target nucleic acid, said polystyrene sulfonic acid having a molecular weight of between about 1,000 and 1,000,000 daltons complementary polynucleotides.

9. The hybridization buffer as claimed in claim 8, wherein the polystyrene sulphonic acid is present in the form of a salt.

10. The hybridization buffer as claimed in claim 8, wherein polystyrene sulphonic acid of molecular weight from 60000 to 80000 is present at a concentration of 1 to 10%.

11. The hybridization buffer as claimed in claim 9, wherein dextran sulphate is present at a concentration of 0.1 to 10%.

12. The hybridization buffer as claimed in claim 9, wherein polyethylene glycol is present at a concentration of 1 to 25%.

13. A hybridization buffer as claimed in claim 9, wherein a cationic detergent is present to reduce non-specific binding at a concentration of 0.02 to 2.0%.

14. The hybridization buffer as claimed in claim 13, wherein the cationic detergent is cetyl trimethylammonium bromide or cetyl pyridinium chloride.

* * * * *

Adverse Decisions in Interference

Patent No. 5,512,436, Timothy Stone, ENHANCEMENT OF POLYNUCLEOTIDE HYBRIDIZATION, Interference No. 103,849, final judgment adverse to the patentee rendered January 30, 1998, as to claims 1-14.

*(Official Gazette May 25, 1999)*

Adverse Decisions in Interference

Patent No. 5,512,436, Timothy Stone, ENHANCEMENT OF POLYNUCLEOTIDE HYBRIDIZATION, Interference No. 103,849, final judgment adverse to the patentee rendered January 30, 1998, as to claims 1-14.

*(Official Gazette June 8, 1999)*